US005133741A

United States Patent [19]

Filho

[11] Patent Number: 5,133,741

[45] Date of Patent: Jul. 28, 1992

[54] THERAPEUTIC TABLE FOR THE TREATMENT OF SPINAL AILMENTS

[76] Inventor: Pedro L. Filho, n188 Alameds dos Maracatins, Sao Paulo, Brazil, 04089

[21] Appl. No.: 655,460

[22] PCT Filed: Aug. 17, 1989

[86] PCT No.: PCT/BR89/00011

§ 371 Date: Feb. 12, 1991

§ 102(e) Date: Feb. 12, 1991

[87] PCT Pub. No.: WO90/03770

PCT Pub. Date: Apr. 19, 1990

[30] Foreign Application Priority Data

Oct. 12, 1988 [BR] Brazil .................................. 6802284

[51] Int. Cl.[5] .............................................. A61F 5/00

[52] U.S. Cl. .................................... 606/242; 606/245; 5/633; 5/614

[58] Field of Search ............................ 128/71, 72, 70; 269/322-325

[56] References Cited

U.S. PATENT DOCUMENTS 1,499,013 3/1923 Gunther ............................... 128/72

3,806,109 4/1974 Weber ................................ 269/323

3,866,899 2/1975 Lee .................................... 269/322

FOREIGN PATENT DOCUMENTS 8301379 4/1983 World Int. Prop. O. .......... 269/324

*Primary Examiner*—Richard J. Apley

*Assistant Examiner*—Susan L. Weinhoffer

*Attorney, Agent, or Firm*—Cohen, Pontani, Lieberman & Pavane

[57] ABSTRACT

The present invention relates to a therapeutic table for the treatment of spinal ailments which consists of a horizontal platform or table divided into three segments. An upper segment supports the patient's torso and head, a center segment supports the pelvic region of the patient and a lower segment supports the legs of the patient. The patient, while lying on his or her back, is securedly strapped to the upper and center segments, whereupon the center segment is caused to move upward diagonally at approximately a 45 degree angle. This linear, angled motion, which is reciprocally repeated, results in simultaneous arching and tractioning of the patient's spine, thereby decompressing the vertebrae and providing therapeutic treatment.

7 Claims, 3 Drawing Sheets

THERAPEUTIC TABLE FOR THE TREATMENT OF SPINAL AILMENTS

FIELD OF THE INVENTION

The present invention relates to a therapeutic table which is useful for the treatment of spinal ailments. The table is equipped with a movable center portion oriented under the pelvis of a patient, who would normally lie supine on the table. The center portion is securably attached to the pelvis of the patient and linearly movable at an angle to the substantially horizontal orientation of the table. When so moved, it imparts arching and tractioning of the patient's spine and pelvis in a comfortable and therapeutic manner.

BACKGROUND OF THE INVENTION

Many frequently occurring physical problems today, such as muscular, sciatic and/or neuralgic pains, are directly related to the displacement of the pelvis at the level of the sacrum-lumbar articulation. This displacement, often caused by accidents, falls or excessive weight being carried with improper posture, causes a distortion of the skeleton and consequently alters the neuralgic network, which results in the previously mentioned physical problems. In such cases, the basic treatment and recuperative regimen for the patient is to correct the displacement of the pelvis, which is currently done through manual manipulations or through orthopedic tables with manual, hydraulic or pneumatic drives.

Manually operated orthopedic tables, while often useful in the treatment of the patient's spinal column, present the disadvantage during use of demanding a high level of physical effort from the physician or therapist in the simultaneous movement and force control of the movable seats commonly associated with such manual tables.

Hydraulic, manually driven orthopedic tables which impart vertical and horizontal movement to the patient, reduce somewhat the disadvantages of manually driven tables, yet still present various disadvantages such as inadequacy of the mechanical elements to perform all of the manipulative functions required. The complexity of the mechanism lends to the difficulty of its manufacture, increasing production costs, as well as increasing the number of articulating and movable mechanical elements. This yields a piece of equipment of excessive weight which demands frequent maintenance. Additionally, in order to provide appropriate therapy to the patient and to meet the requirements inherent to spinal column therapy—mainly to treat the problem of sciatic and lumbar pains—the physician must manually move a platform and pump unit, as well as the pistons, before the seat may be moved to the proper position. Additionally, these tables are typically over-designed, having a weight capacity up to five times that normally required to treat a patient, which also contributes to the high cost of the equipment.

Pneumatically driven orthopedic tables may produce horizontal and/or vertical movement in the patient and overcome some of the difficulties of a manually driven table, however, other disadvantages still exist. For example, in piston drives which arch the lumbar column, the arching results in certain discomfort and even pain. Since this area of the spinal column is the critical location of the ailment, the mere and simple arching can induce muscular contractions in the patient which are pain inducing. In tables which can move horizontally and vertically, the mechanisms are greatly complicated, requiring multiple pistons and other linkages and components in order to perform adequately.

It would therefore be greatly advantageous to provide a table which can induce the proper movement in the patient's pelvis and spine to treat the above-mentioned problems while utilizing a simplified, hydraulic drive system which results in reduced manufacturing cost and fewer maintenance problems. Such a table would simultaneously arch and traction the spinal column of the patient, reducing or eliminating undesired muscular contractions which cause pain and hinder treatment.

OBJECTS AND SUMMARY OF THE INVENTION

The instant invention relates to a table for use in the treatment of spinal ailments which, through a simple mechanism, can impart therapeutically proper motion to the patient's pelvis and achieve the correct balance of arching and tractioning of the spine which is commonly needed to properly treat such ailments. The table, upon which a patient would lie face up, is segmented into three parts, an upper segment supporting the head and torso, a center segment supporting the pelvic region of the patient, and a lower segment supporting the legs of the patient. The upper segment is guidedly movable along the horizontal plane. The center segment is movable along a vertical plane at an angle of 45 degrees, and the lower segment is typically fixed in the horizontal plane, but may fold downward when not in use to save space. When in operation, the patient's torso is secured to the upper segment and the patient's pelvis is secured to the center segment. When the table is activated, the center segment moves upwardly at a 45 degree angle which causes the patient's pelvis to move up and away from the upper segment which securedly holds the patient's torso. This lifting up and away arches the back of the patient, while simultaneously, since the motion is angled, tractions the spine and decompressing the vertebrae, providing the patient the required relief. The center section is then returned to its original position. This reciprocal motion may be repeated as many times as deemed necessary by the therapist or physician.

The upper segment is allowed to move in response to the motion of the center segment but is restrained by springs which dampen the tractioning of the patient's spine as the center segment goes through its full range of angled linear movement.

It is therefore an object of this invention to provide a therapeutic table, useful in the treatment of spinal ailments, which can simultaneously arch and traction a patient's spine so as to decompress the vertebrae without inducing muscular contractions or other pain.

It is a further object of this invention to provide a therapeutic table, useful in the treatment of spinal ailments, which is mechanically driven and easy to operate.

It is a further object of this invention to provide a therapeutic table, useful in the treatment of spinal ailments, which is efficient to manufacture and maintain.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DESCRIPTION OF THE DRAWING FIGURES

In the drawings, wherein like reference characters denote similar elements throughout the several views.

DETAILED DESCRIPTION OF THE PRESENTLY PREFERRED EMBODIMENTS

Figure 1:
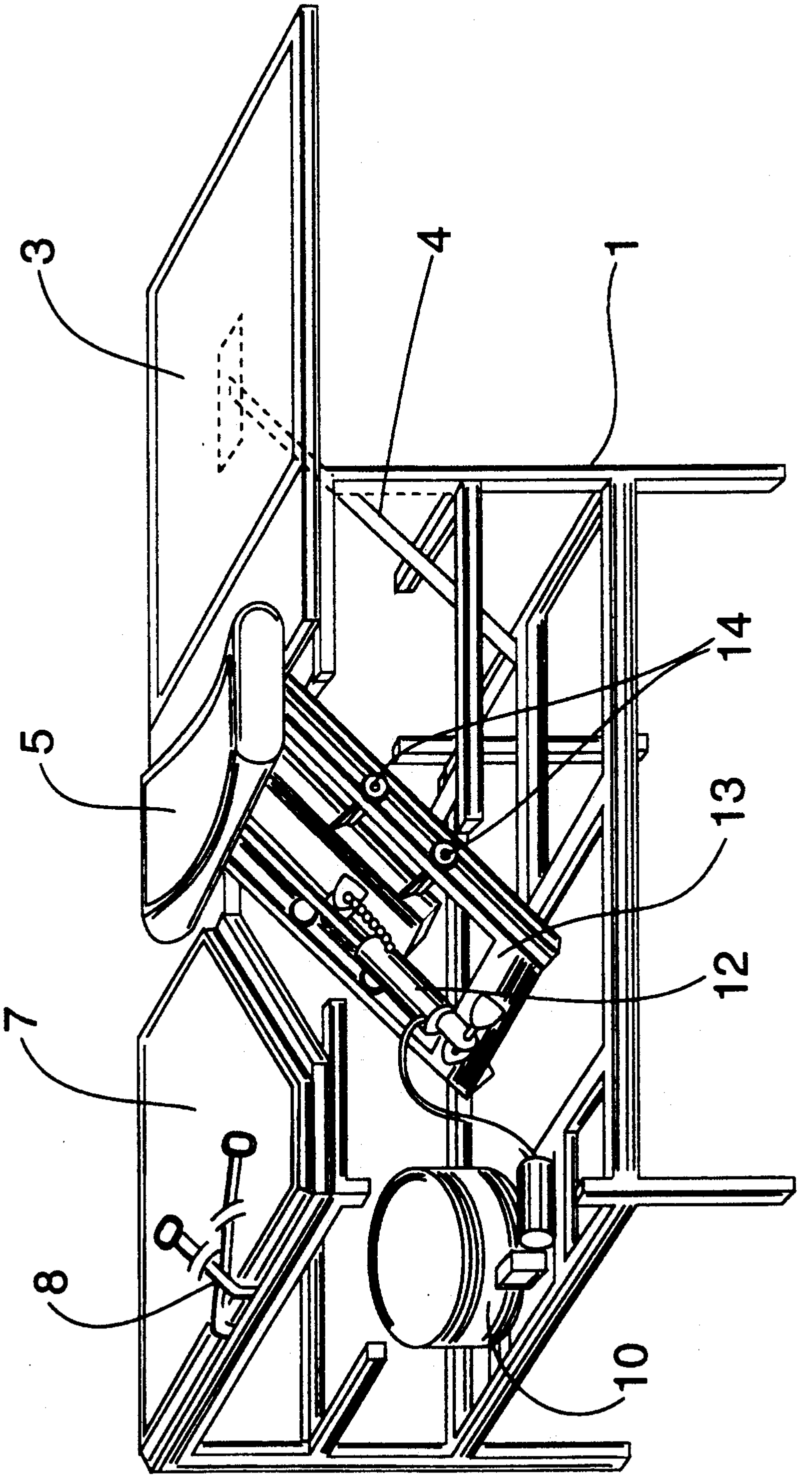
FIG. 1 shows a perspective side elevation of the subject treatment table with partial cutaways revealing details of the center segment.
Figure 2:
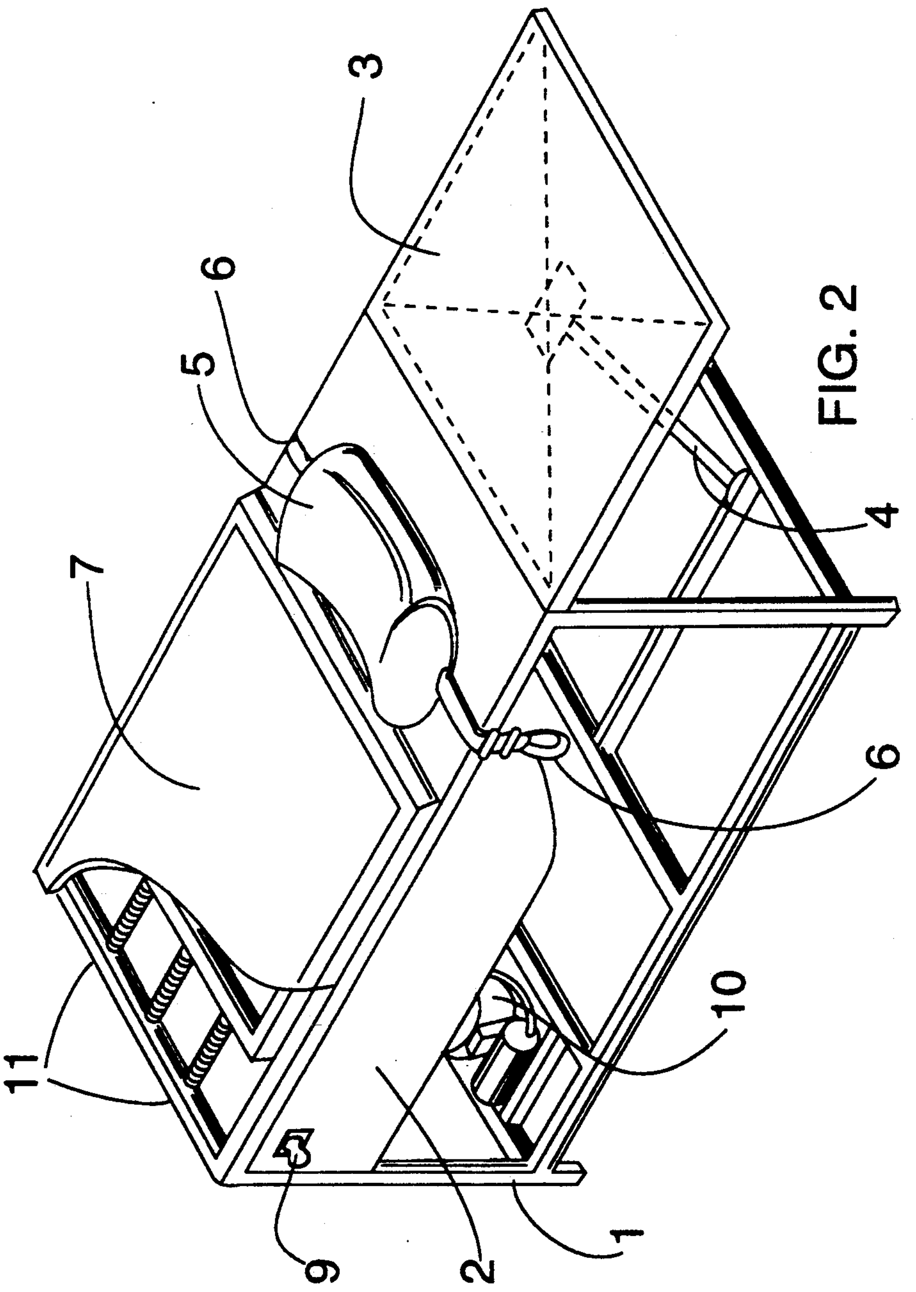
FIG. 2 is a side view, in perspective, showing the lower segment in folded down position.

With initial reference to FIG. 1, the therapeutic table 1 of the instant invention is shown in side view. The table 1 is constructed of a frame, preferably metal, and substantially horizontal segments, preferably of plywood, upon which a patient would lie supine. The patient is oriented so that the patient's head and back are supported on an upper segment 7, the pelvic region of the patient is oriented so as to lie on a center segment 5, and the patient's legs are supported by a lower segment 3. The lower segment 3 may be adapted so as to be foldable and supported on a swinging support arm 4, which would allow for the lower segment to be swung down and away when the table is not in use, as shown in FIG. 2.

The patient is secured to the table via straps or belts 8 which secure the patient's torso to the upper segment, and straps or belts 6 which secure the patient's pelvis to the center segment 5. The upper, lower and center segments are configured as flat plates which may be made of wood, but and are covered with cushioned fabric for increased patient comfort while the patient lies on the table. Center segment 5 may also be curved or formed so as to better conform to the shape of the human pelvic region and thereby improve patient comfort and increase the security of the fastening belts 6 which secure the patient's pelvis to the center segment 5.

Referring again to FIG. 1, an exemplary drive mechanism 12, for imparting angled, linear motion to center segment 5, is shown. A frame which serves as a support base 13 for center segment 5 is oriented within the central body of the table 1 and under the center segment 5. Base 13 is mounted at an angle, preferably approximately 45 degrees from the horizontal plane of the table surface, and supports a piston 12, preferably a hydraulically driven piston, served by motor pump unit 10. Center segment 5 is so mounted as to be guidedly driven by piston 12 for angled linear movement along base 13 via bearings 14. Drive system 10—which may be actuated by a key switch 9—is covered for patient safety by a shield plate 2, which also covers the piston 12 and base 13.

Figure 3:
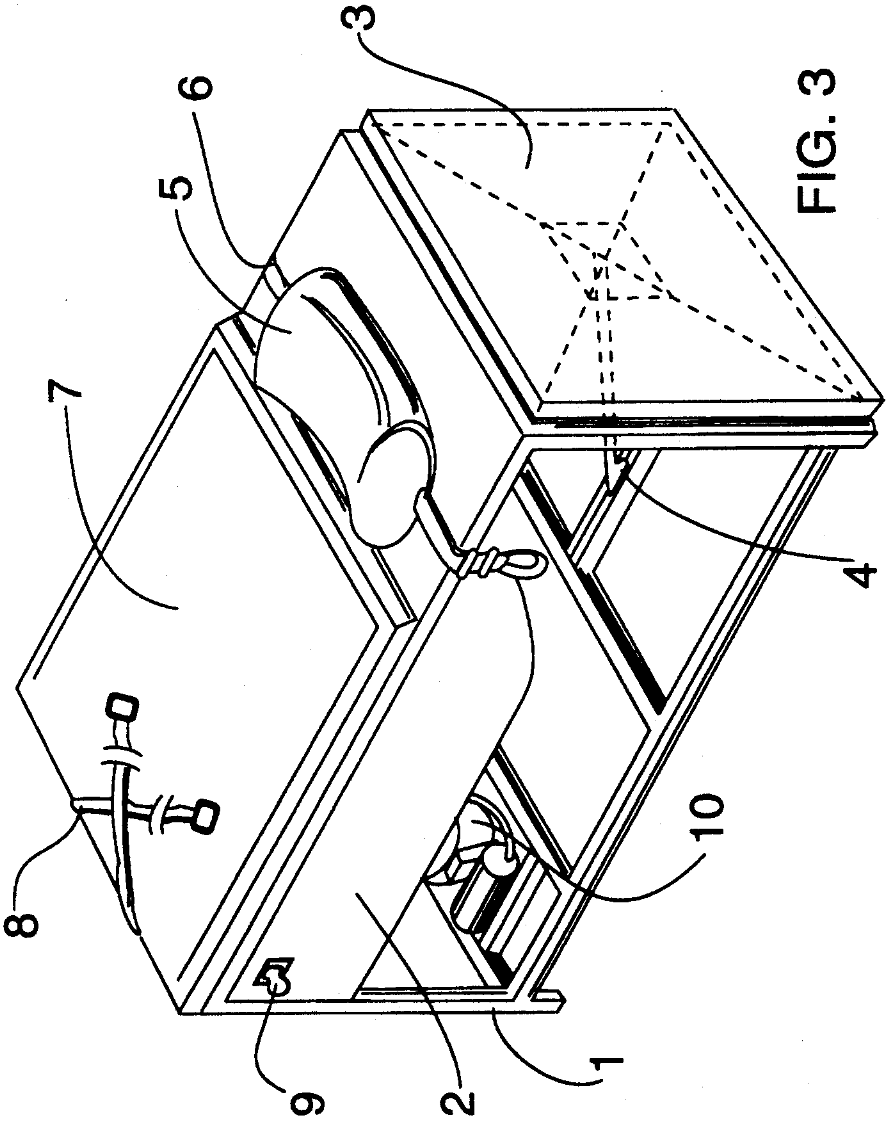
FIG. 3 Is a side perspective view showing a partial cutaway of the movable upper segment.

Referring now to FIG. 3, the upper segment 7 is shown in partial cutaway, revealing springs 11 which restrain the horizontal movement of the upper segment 7 as the upper segment moves back and forth in the horizontal plane along the surface of the table 1.

In operation, the patient is securely fastened via belts 8 and 6 to the upper segment 7 and center segment 5, respectively. Lower segment 3 is typically extended and supported via support arm 4 to extend the horizontal plane of the table and support the patient's legs during operation. Once the patient is properly positioned and secured, the physician or therapist actuates drive system 10 via key switch 9, which causes piston 12 to drive center segment 5 upward along a linear path at approximately 45 degrees from the horizontal. During therapy, a typical displacement for center segment 5 would be approximately 160 mm. As a result of the diagonal movement of the center segment 5 at approximately a 45 degree angle, the pelvis of the patient, which is secured to center segment 5, is simultaneously lifted and moved away from the torso which is secured to upper segment 7. This diagonal, upward motion simultaneously arches and tractions the spinal column of the patient, decompressing the subject vertebrae. Upper segment 7, which is horizontally movable, albeit partially restrained by springs 11, moves back and forth horizontally in response to the motion imparted to the patient's body by center segment 5. Springs 11 act to dampen the tractioning of the patient's spine imparted by the motion of center segment by partially restraining the horizontal movement of upper segment 7. This gentle arching and lifting of the patient's pelvis and back, which occurs simultaneously, tractions the spine and decompresses the vertebrae with minimal discomfort or pain to the patient.

After center segment 5 has fully extended, the piston retracts, returning center segment 5 to its original position. This reciprocal angled movement of center segment 5 is repeated as often as is deemed necessary by the physician or therapist, depending on the degree of severity of the physical problem present in the patient. Treatment time using the apparatus of the instant invention is greatly reduced, since, in conventional tables, a typical cycle of traction and relaxation takes approximately 30 seconds, where with the proposed table this cycle is approximately halved.

Additionally, through the relatively simple nature of the drive and the construction thereof, the table of the instant invention can be manufactured at lower cost and in less time, as well as be easily maintained.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, however, therefore, to be limited only as indicated by the scope of the claims appended hereto.

What is claimed is:

1. A tractioning apparatus for treating ailments of the spine in a human patient; said apparatus comprising:
   - a segmented table defining a substantially horizontal patient support plane for supporting a human body in a supine position along said plane of said table, said segmented table comprising:
   - an upper segment for supporting the torso and head of the body, said upper segment being guidedly, bi-directionally movable along said horizontal plane;
   - a lower segment for supporting the legs of the body; and
   - a center segment operatively positioned between said upper and said lower segments for supporting the pelvic region of the body, said center segment being mounted for movement relative to said upper and lower segments;

means for securing the torso of the body to said upper segment;

means for securing the pelvic region of the body to said center segment;

means for imparting reciprocal, linear motion to said center section in first and second selectively opposite directions at an angle between the horizontal and vertical planes table and respectively away from and toward said upper segment so that when said first direction linear motion is imparted to said center section, the pelvic region of the body is lifted upwardly from said horizontal plane of said table and away from said upper segment so as to simultaneously arch and tractionally stretch the body and, thereby, the pelvis and spine, said upper section guidedly moving along said horizontal plane in response to said motion of said center segment; and means for resiliently restraining said guided, bi-directional movement of said upper segment in said horizontal plane, so as to operatively dampen the tractional stretch of the body imparted by said motion of said center segment.

2. The apparatus according to claim 1, wherein said reciprocal linear motion of said center segment is imparted along a vertical plane at an angle of approximately 45 degrees to the substantially horizontal plane of the table.

3. The apparatus according to claim 1, wherein said lower segment further comprises means for adjustably positioning at least a portion of said lower segment at an angle to said substantially horizontal plane of said table.

4. The apparatus according to claim 1, wherein said motion imparting means comprises a key-actuated, hydraulic drive.

5. The apparatus according to claim 1, wherein said securing means comprises adjustable belts.

6. The apparatus according to claim 1, further comprising a resilient, cushion-like material covering at least one of said upper, center, and lower segments so as to substantially conform to the shape of a human body as it is supported on said table.

7. The apparatus according to claim 1, wherein said center segment is contoured so as to substantially conform to the shape of the pelvic region of the body.

* * * * *